(«12») United States Patent
Perraut et al.

(10) Patent No.: US 6,893,876 B2
(45) Date of Patent: May 17, 2005

(54) ENHANCING SURFACE-GENERATED FLUORESCENCE SIGNAL EMITTED BY A SAMPLE

(75) Inventors: François Perraut, Saint Joseph de Riviere (FR); Patrick Chaton, Theys (FR); Patrick Pouteau, Voreppe (FR)

(73) Assignees: Commissariat a l'Energie Atomique, Paris (FR); BioMerieux SA, Marcy l'Etoile (FR)

( * ) Notice: Subject to any disclaimer, the term of this patent is extended or adjusted under 35 U.S.C. 154(b) by 0 days.

(21) Appl. No.: 10/129,948

(22) PCT Filed: Dec. 1, 2000

(86) PCT No.: PCT/FR00/03359

§ 371 (c)(1),
(2), (4) Date: May 17, 2002

(87) PCT Pub. No.: WO01/40778

PCT Pub. Date: Jun. 7, 2001

(65) Prior Publication Data

US 2002/0171045 A1 Nov. 21, 2002

(30) Foreign Application Priority Data

Dec. 2, 1999 (FR) .............................. 99 15193

(51) Int. Cl.$^7$ .............................................. G01N 21/64
(52) U.S. Cl. ..................................... 436/172; 422/82.08
(58) Field of Search ....................... 436/172; 422/82.05, 422/82.08, 82.11; 250/458.1, 459.1

(56) References Cited

U.S. PATENT DOCUMENTS

| 4,649,280 A | * | 3/1987 | Holland et al. ........... 250/483.1 |
| 5,082,629 A | * | 1/1992 | Burgess et al. ........... 422/82.11 |
| 5,552,272 A | * | 9/1996 | Bogart ......................... 435/6 |
| 5,822,472 A | * | 10/1998 | Danielzik et al. .............. 385/12 |

FOREIGN PATENT DOCUMENTS

| WO | 90 06503 | 6/1990 |
| WO | WO 9006503 | * 6/1990 |

* cited by examiner

Primary Examiner—Jeffrey R. Snay
(74) Attorney, Agent, or Firm—Oblon, Spivak, McClelland, Maier & Neustadt, P.C.

(57) ABSTRACT

A device and process for the amplification of fluorescence emitted by an areal sample. The device includes a support transmitting all or part of a fluorescence signal and configured to support the areal sample and a thin layer interposed between the support and the areal sample. The thin layer has a refractive index greater than the refractive index of the support and than the refractive index of a medium flooding the areal sample during a fluorescence measurement. The thickness of the thin layer is chosen so that the thin layer transmits all or part of the fluorescence signal which is measured after passing through the support.

12 Claims, 1 Drawing Sheet

ENHANCING SURFACE-GENERATED FLUORESCENCE SIGNAL EMITTED BY A SAMPLE

FIELD OF THE INVENTION

The present invention relates to a process for amplifying a fluorescence signal emitted by an areal sample supported by a support in response to an excitation signal. It also relates to a device amplifying the fluorescence emitted by such a sample.

PRIOR ART

Measurement by fluorescence is a method of measurement used in many technical fields. It is used particularly to operate devices of chemical and/or biological analysis known by the name of bio-chips. Measuring biological activity with a chip of this kind is done by measuring the fluorescence emission of a molecule fixed to the biological sample, which is presented in the form of a surface coating, using for example an epifluorescence microscope, a scanner, a fluorimeter. To make the measurement, the chip may be placed in a special chamber or cartridge. It may also be placed directly on the bottom of a Petri dish. It may again be placed in the air using a mechanical support. In some cases, the areal sample is read in the so-called rear surface mode, in other words the reading is taken by passing through a support supporting on one of its surfaces the areal sample, the support being necessarily transparent to the fluorescence signal.

The fluorescence excitation signal is generally directed towards the sample through its support, which is to advantage in the shape of a lamina. Another way of exciting fluorescence is to generate evanescent waves by injecting the excitation light through the slice of the lamina or by making a coupling via a prism.

In other cases the areal sample is read in the so-called front surface mode, the reading being taken directly on the areal sample placed on the support.

The areal sample may be constituted from a biospecific surface formed on one surface of the support and acting as a capture phase to a body carrying a fluorescent marker. It is thus possible to form a complex, for example a nucleic acid duplex. The biospecific surface may be made by a combinatorial synthesis of probes, by depositing probes using a projection technique or in some other way. This complex may also be an antibody-antigen association, the antibodies deposited on the surface of the support forming the biospecific surface. The thickness of the surface forming the complex is between a few nanometers and a few hundred nanometers. The complex may also be brought onto the surface after its formation, for example by drying or adsorption of the complex on the support surface.

The first mention of the possibility of obtaining an enhancement of fluorescence is given in the article entitled "Model for Raman and fluorescent scattering by molecules in small particles" by H. CHEW et al. Physical Review A, 13(1), pp 396 to 404, 1976. This article, which deals simultaneously with Raman scattering and fluorescence, concerns a theoretical model which establishes that the field irradiated by a fluorescent molecule is not isotropic when it is placed in a spherical body (cell, aerosol drop). The theoretical model describes only the angular distribution of light emission but does not conclude on the possibility of applying this principle in order to obtain greater sensitivity.

More recently, a model dedicated to fluorescence, but with a different physical formalisation, was proposed by J. ENDERLEIN et al. in an article entitled "Highly efficient optical detection of surface generated fluorescence", Applied Optics, Vol. 38, No 4, 1999, pp 724 to 732.

A review of the phenomena of molecular fluorescence near interfaces was established by R. R. CHANCE et al. in "Molecular fluorescence and energy transfer near interfaces", Advanced in Chemical Physics, vol XXXVII, pp 1 to 65—Prigogine I., Rice S. R., 1978. This review deals only with the phenomena of ionised molecule relaxation time and variations in apparent quantum yields. If a calculation model is presented for dielectric stacks, it also only relates to the phenomena of ionised molecule relaxation time and variations in apparent quantum yields. Lastly, it is supposed that fluorescence emission is isotropic in space, which is not the case.

D. A. WEITZ et al., in an article entitled "The enhancement of Raman scattering, resonance Raman scattering and fluorescence from molecules adsorbed on a rough silver surface", Journal of Chemical Physics, 79(9), pp 5324 to 5338, 1983, propose a model well adapted to the fluorescence emission of molecules deposited on a rough surface or on a plane surface on which islands of colloidal silver have been deposited. Experiments have been conducted and fully validate the model. According to this design, the fluorescence reading can only be taken on the front surface. The physical phenomenon implemented here is an electromagnetic coupling between a plasmon resonance on the surface of the colloidal silver to create a very intense local electromagnetic field and the fluorescent molecules. The gain in fluorescence is then a function of the position of the molecules relative to the islands of silver. If there is contact, the molecules are adsorbed on the surface and the fluorescence is inhibited as is indicated in the article by K. SOLOKOV et al., entitled "Enhancement of molecular fluorescence near the surface of colloidal metal film", Analytical Chemistry, Vol. 70, No 18, pp 3898 to 3905, 15 Sep. 1998.

International application WO-A-9-9/23 492 discloses a technique for amplifying fluorescence which makes use of a surface likely to enhance fluorescence, this surface being interposed between a support and the biological complex deposited on the support, the measurement being taken through the support. This intermediate surface must however be textured and, to this end, the material forming this surface is chosen from among nylon membranes, material and texture causing the scattering of the fluorescence signal, a phenomenon that the invention avoids.

The document U.S. Pat. No. 5,822,472 discloses a process for detecting luminescence excited evanescently. The process uses a transparent substrate supporting a transparent layer forming a wave guide. The transparent layer material has a refractive index greater than the refractive index of the transparent substrate material. The device also has two coupling networks. One of these networks makes it possible to introduce a luminous excitation beam, passing through the transparent substrate, into the transparent layer. The excitation beam is conveyed via the transparent layer forming a wave guide. Substances in contact with the transparent layer and having luminescent properties are then excited in the evanescent field of the layer forming the wave guide. The coupling network ensures the emergence of the excitation beam from the transparent layer, the emergent beam then passing through the transparent substrate. The transparent layer forming the wave guide has a thickness smaller than the wavelength of the excitation light. Its refractive index is $\leq 1.8$. The excitation beam is then conveyed via the transparent layer between a beam insertion area and a beam emergence area (the coupling networks). Guiding the beam via the transparent layer necessarily entails a loss of part of the fluorescence signal.

DISCLOSURE OF THE INVENTION

The invention proposes another way of obtaining the amplification of a fluorescence signal while avoiding the drawbacks of the methods or devices of the prior art.

The invention makes use of the fact that molecules placed on a surface constitute a discontinuity in the refractive index and that they emit the greater part of their fluorescence in the medium which has the highest index. The angular distribution of fluorescence of surface molecules is very different from that of molecules in the volume. In the case of a liquid, it is considered that fluorescent emission is isotropic since the fluorescent molecules are not orientated relative to each other (random distribution of orientation of dipole moments). The phenomenon is different when the fluorescent molecules constitute a thin layer of a few tens of nanometers to a few hundred nanometers. The signal emitted in fluorescence is a function of the orientation of the electric dipoles constituted by the fluorescence molecules. It is therefore favourable, for surface fluorescence, to arrange the fluorescent molecules at the interface of two media of very different refractive index.

The excitation and fluorescence signals pass in almost normal incidence through the thin layer, which is not then used as a wave guide. There cannot therefore be any loss of part of the fluorescence signal.

It is therefore possible to use a material with a high refractive index in the form of a layer thin enough to be transparent to the fluorescence signal, this thin layer being supported by a support transparent to the fluorescence signal.

It may also be possible to use a thin layer consisting of a stack of sub-layers of different materials, this thin layer having the same optical properties as the previous thin layer, particularly as regards the refractive index and transparency to the fluorescence signal.

A first objective of the invention is a process for amplifying a fluorescence signal emitted by an areal sample supported by a support in response to an excitation signal, the support transmitting all or part of the fluorescence signal, consisting in interposing a thin layer between the support and the areal sample, the thin layer having a refractive index greater than the refractive index of the support and than the refractive index of the medium flooding the areal sample, the thickness of the thin layer being selected in such a way that the thin layer transmits all or part of the fluorescence signal which is measured after passing through the transparent support.

The areal sample may be supported by a support made of a material selected from glass, quartz, silica, plastic materials such as polystyrene, polypropylene, polycarbonates, polymethylmetacrylates.

The process may consist in interposing, between the support and the areal sample, a thin layer of a material chosen from silicon nitride, silicon carbide, titanium oxides, aluminium oxide, $ZrO_2$, $ZrO_4Ti$, $HfO_2$, $Y_2O_3$, diamond, MgO, oxynitrides ($Si_xO_yN_z$) fluorinated materials such as $YF_3$ or $MgF_2$. This thin layer may also be obtained by stacking several sub-layers whose optical properties and thickness confer on the whole represented by the latter the necessary characteristics (see A. HERPIN, C. R. Acad. Sciences, Paris, 225, 182, 1947).

The thin layer may be a layer obtained on the support by one of the following methods: vapour deposition, replication, transfer, film deposition, by processes of the CVD type (LPCVD, PECVD etc.) or of the PVD type, by film transfer, by the sol-gel process. It may be a layer transferred onto the support by one of the following methods: bonding and molecular adhesion.

Possibly, said thin layer obtained on the support may be annealed.

The areal sample may consist of a complex associating a biospecific surface with sample molecules carrying a fluorescent marker.

The medium flooding the sample may be a liquid, a gel or a gas.

A second objective of the invention is a device amplifying the fluorescence emitted by an areal sample via one of the processes above, the device including a support transmitting all or part of the fluorescence signal and intended to support the areal sample, a thin layer of a material being interposed between the support and the areal sample, the thin layer material having a refractive index greater than the refractive index of the support and than the refractive index of the medium flooding the areal sample during a measurement of fluorescence, the thickness of the thin layer being chosen so that the thin layer transmits all or part of the fluorescence signal which is measured after passing through the support.

A third objective of the invention consists of a biochip, characterised in that it includes the device above, the device supporting a plurality of areal samples constituting as many recognition zones.

BRIEF DESCRIPTION OF THE DRAWINGS

The invention will be better understood and further advantages and particularities will emerge from reading the following description, given as a nonrestrictive example, accompanied by the appended drawings among which.

DETAILED DESCRIPTION OF EMBODIMENTS OF THE INVENTION

The invention consists in interposing a thin layer between a support transparent to the fluorescence signal and an areal sample plunged into a medium and in measuring the fluorescence through the support.

The material constituting the thin layer is selected in such a way that its refractive index is greater than the refractive index of the material constituting the support and greater than the refractive index of the medium flooding the areal sample.

The medium flooding the areal sample is for example a liquid buffer if total control of the medium in respect of fluorescence (pH, salinity) is required. The medium may be a gel if it is desired to reduce photodestruction or "bleaching" of the fluorescent molecules. This medium may also be a gas (air, or neutral gas) if the fluorescent complex requires such reading conditions.

By way of example, the support is a 700 µm thick silica lamina ($SiO_2$) with a refractive index of 1.485 to 650 nm. The thin layer may be a 150 nm thick layer of silicon nitride ($Si_3N_4$) with a refractive index 1.997 for the same wavelength. The areal sample may be a DNA based complex marked with a fluorescent cyanine (Cy5-Amersham, trademark). The medium flooding the sample may be constituted by a liquid washing buffer (0.005% SSPE 6X/Triton X-100), with an index of 1.34. For such a device, 60% fluorescence amplification is measured relative to the measurement taken in the same conditions for the complex deposited directly onto the support, without the presence of the thin layer. The measurement is taken with an epifluorescence microscope and a CCD camera. Fluorescence excitation is centred on 635 nm and measurement of the emission is centred on 670 nm. The value of the gain is a function of the measurement system (wavelength, optical numerical aperture), the marker used (dipole moment orientation) and the characteristics of the thin layer (refractive index, thickness).

Figure 1:
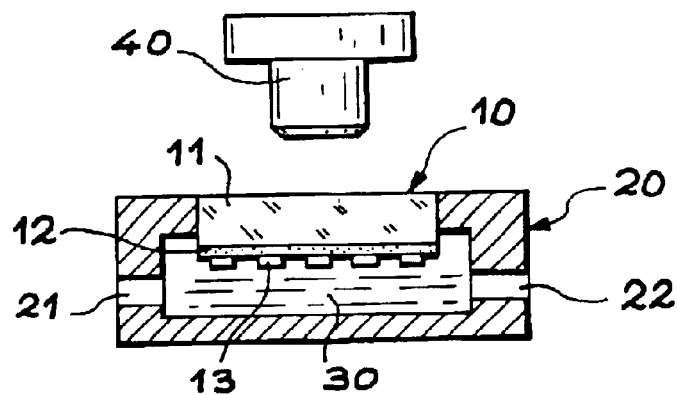
FIG. 1 shows a device according to the present invention in a first configuration of reading a fluorescence signal.

FIG. 1 shows a device according to the invention placed in a casing in order to carry out the fluorescence measurement. The device 10 is constituted by a lamina-shaped transparent support 11 coated on one of its surfaces with a thin layer 12. An areal sample 13 is deposited on the free surface of the thin layer 12. The device 10 is for example constituted by the elements described above.

The device 10 is placed, for the measurement of fluorescence, in a housing provided in the upper wall of a casing 20. It is placed in such a way that the areal sample 13 faces towards the inside of the casing 20. The casing has an input orifice 21 and an output orifice 22 and so as to bring the areal sample into contact with a liquid 30 constituting the medium flooding the areal sample.

The fluorescence signal is picked up by a measuring instrument 40. As is well shown in FIG. 1, the fluorescence signal reaches the measuring instrument 40 by passing through the thin layer 12 and the transparent support 11. This is the so-called rear surface reading mode.

Figure 2:
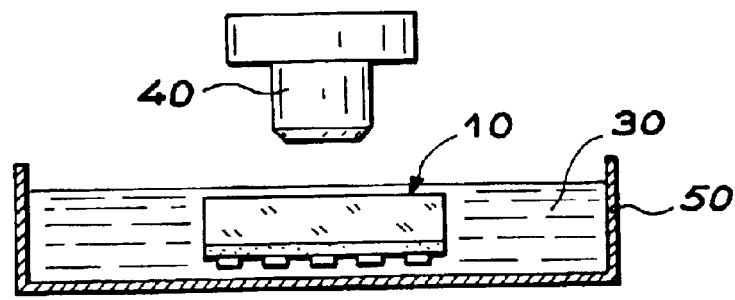
FIG. 2 shows a device according to the present invention in a second configuration of reading a fluorescence signal.

FIG. 2 shows the same device 10 placed on the bottom of a Petri dish 50 containing the medium 30. The fluorescence reading is also taken on the rear surface using the measuring instrument 40.

Figure 3:
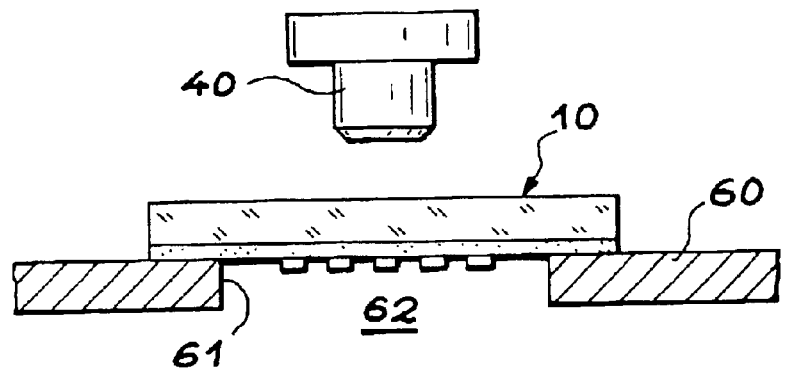
FIG. 3 shows a device according to the present invention in a third configuration of reading a fluorescence signal.

FIG. 3 shows the same device 10 placed in the air to take the fluorescence measurement. The device 10 is held by its periphery by means of a mechanical support including a slide 60 pierced with an aperture 61 allowing the areal sample to be in contact with the air 62.

The support may be a glass, silica or polystyrene slide. It is transparent for the spectral domain of the fluorescence measurement. The thin layer deposited on one surface of the support may be made by vapour deposition or by replication (optical thin layer technology) for materials like silicon nitride, titanium oxide, aluminium oxide. It may be deposited in the form of a film or transferred onto the support (by bonding, by molecular adhesion) in the case of a thin layer of a thickness greater than a few $\mu$m.

Different experiments have been conducted to demonstrate the efficiency of the invention. The experiments related to several devices:
a glass support in accordance with the known art, in other words without a fluorescence amplifying thin layer,
a device according to the invention with the thin layer being of silicon nitride,
a device according to the invention with the thin layer being of annealed silicon nitride (annealing in nitrogen allows the nitride layer to density).

The fluorescence reading was taken by means of an epifluorescence microscope equipped for the Cy5 marker and by means of a cooled digital CCD camera. Two measurements were taken per device: one measurement on the front surface and one measurement on the rear surface. The measurement on the front surface is taken by placing the areal sample opposite the measuring instrument, the fluorescence signal then not passing through the support or the device.

The measurements taken show an enhancement of fluorescence by 1.6 times for a device with a thin layer of $Si_3N_4$ relative to a simple glass support, and an enhancement of fluorescence by 2.4 times for a device with a thin layer of $Si_3N_4$ subjected to an anneal relative to the simple glass support.

The device of the invention may be used in a biochip comprising a plurality of zones of molecular recognition. By biochip is understood a chip or a support having on its surface one or more zones, so-called recognition zones, equipped with molecules having recognition properties. The recognition molecules may be, for example, oligonucleotides, polynucleotides, proteins such as antibodies or peptides, lectins or any other system of the ligand-receptor type. In particular the recognition molecules may comprise fragments of DNA or RNA.

When the biochip is brought into contact with a sample for analysis, the recognition molecules are likely to interact, for example by complexation or by hybridisation with molecules called "target molecules" of the sample. In this way, in equipping a biochip with a plurality of recognition zones with different recognition molecules selectively sensitive to different target molecules, it is possible to detect and possibly to quantify a great variety of molecules contained in the sample.

The complexes formed on the biochip can be identified by means of a fluorescent marking applied to the target molecules of the sample. In this way, the biochip support is the support of the invention device coated with the thin layer and the recognition zones of the biochip are the areal samples.

What is claimed is:

1. A process for amplifying a fluorescence signal emitted by an areal sample supported by a support in response to an excitation signal, the support transmitting all or part of the fluorescence signal, comprising:
   interposing a thin layer between the support and the areal sample,
   wherein the thin layer has a refractive index greater than a refractive index of the support and than a refractive index of a medium flooding the areal sample,
   a thickness of the thin layer being selected so that the excitation and fluorescence signals pass in almost normal incidence through the thin layer, whereby the thin layer transmits all or part of the fluorescence signal which is measured after passing through the support.

2. A process according to claim 1, wherein the support supporting the areal sample is made of a material selected from glass, quartz, silica, or plastic materials selected from polystyrene, polypropylene, polycarbonates, polymethylmethacrylates.

3. A process according to claim 1, wherein the thin layer interposed between the support and the areal sample is of a material chosen from silicon nitride, silicon carbide, titanium oxides, aluminium oxide, $ZrO_2$, $ZrO_4Ti$, $HfO_2$, $Y_2O_3$, diamond, MgO, oxynitrides ($Si_xO_yN_z$), fluorinated materials, $YF_3$, $MgF_2$.

4. A process according to claim 1, wherein said thin layer is a layer obtained on the support by one of the following methods: vapour deposition, replication, transfer, film deposition by a CVD process, film deposition by a PVD process, by film transfer, by sol gel process.

5. A process according to claim 4, wherein said thin layer is a layer transferred onto the support by one of the following methods: bonding and molecular adhesion.

6. A process according to claim 4, wherein said thin layer obtained on the support is annealed.

7. A process according to claim 1, wherein the areal sample includes a complex associating a biospecific surface with sample molecules carrying a fluorescent marker.

8. A process according to claim 1, wherein the liquid medium flooding the areal sample includes a gel or a gas.

9. A device amplifying fluorescence emitted by an areal sample, the device comprising:
   a support configured to transmit all or part of a fluorescence signal emitted in response to an excitation signal and configured to support the areal sample; and
   a thin layer interposed between the support and the areal sample, the thin layer having a refractive index greater than a refractive index of the support and than a refractive index of a medium flooding the areal sample during a measurement of fluorescence, a thickness of the thin layer being chosen so that the excitation and fluorescence signals pass in almost normal incidence through the thin layer, whereby the thin layer transmits all or part of the fluorescence signal.

10. A biochip for reading by fluorescence, the biochip comprising:
    a support configured to transmit all or part of a fluorescence signal emitted in response to an excitation signal and configured to support a plurality of areal samples constituting as many recognition zones; and
    a thin layer of a material interposed between the support and the areal samples, the thin layer material having a refractive index greater than a refractive index of the support and than a refractive index of a medium flooding the areal sample during a fluorescence measurement, a thickness of the thin layer being chosen so that the excitation and fluorescence signals pass in almost normal incidence through the thin layer, whereby the thin layer transmits all or part of the fluorescence signal.

11. The process according to claim 1, further comprising positioning the support in a casing.

12. The process according to claim 11, wherein the liquid medium is positioned within the casing.

* * * * *